United States Patent [19]

Howard et al.

[11] Patent Number: 5,690,097
[45] Date of Patent: Nov. 25, 1997

[54] COMBINATION ANESTHETIC MASK AND OXYGEN TRANSPORT SYSTEM

[75] Inventors: Gregory L. Howard; Michelle Bowman-Howard, both of Houston, Tex.

[73] Assignee: Board of Regents, The University of Texas System, Austin, Tex.

[21] Appl. No.: 656,387

[22] Filed: May 31, 1996

[51] Int. Cl.⁶ ............................................. A62B 7/00
[52] U.S. Cl. ....................... 128/205.11; 128/204.25; 128/204.29
[58] Field of Search .................. 128/203.12, 203.22, 128/203.23, 203.24, 203.25, 203.28, 204.18, 204.22, 204.23, 202.27, 205.11, 204.29, 911, 912; 137/3, 896

[56] References Cited

U.S. PATENT DOCUMENTS

| | | |
|---|---|---|
| 2,473,518 | 6/1949 | Garrard et al. |
| 2,843,121 | 7/1958 | Hudson. |
| 2,897,833 | 8/1959 | Seeler. |
| 3,316,907 | 5/1967 | Goupil. |
| 3,794,072 | 2/1974 | Diedrich et al. |
| 3,850,171 | 11/1974 | Ball et al. |
| 3,906,996 | 9/1975 | DePass et al. |
| 3,913,607 | 10/1975 | Price. |
| 3,977,432 | 8/1976 | Vidal. |
| 4,036,253 | 7/1977 | Fegan et al. |
| 4,266,540 | 5/1981 | Panzik et al. |
| 4,595,002 | 6/1986 | Michaels et al. |
| 4,848,333 | 7/1989 | Waite. |
| 5,144,945 | 9/1992 | Nishino et al. |
| 5,301,662 | 4/1994 | Bagwell et al. |
| 5,372,129 | 12/1994 | Ryder. |

Primary Examiner—Vincent Millin
Assistant Examiner—Robert N. Wieland
Attorney, Agent, or Firm—Akin, Gump, Strauss, Hauer & Feld, L.L.P.

[57] ABSTRACT

A system to provide supplemental oxygen to a patient via an oronasal mask and an oxygenation adaptor, the adaptor providing for countercurrent flow of fresh (oxygen-enriched) gas and exhaled gas with minimal mixing to reduce oxygen requirements. The Coanda effect is employed to establish and maintain wall attachment of the exhaled gas stream to minimize mixing with incoming fresh gas.

11 Claims, 2 Drawing Sheets

COMBINATION ANESTHETIC MASK AND OXYGEN TRANSPORT SYSTEM

BACKGROUND

FIELD OF THE INVENTION

The invention relates to methods and apparatus for supporting oxygenation in a patient, and in particular for patients being transported.

Oxygenation of patients in transport

Providing supplemental oxygen for spontaneously breathing patients during transport between and within health care facilities is a common safety precaution. Such patients may have impaired pulmonary gas exchange due to lung disease and/or a blunted ventilatory response to carbon dioxide associated with recently administered anesthetics or sedatives. Supplemental oxygen is often administered via a relatively loose-fitting face shield or mask which can raise the avenge fraction of inspired oxygen ($FiO_2$) from about 0.21 (for room air) to about 0.250–0.35. The actual $FiO_2$ attained depends on the patient's minute ventilation and maximum inspiratory flow rate as well as on the flow rate of oxygen used and the adjustment of any air-entrainment dilutor that may be present. Because maximum inspiratory flow rates usually far exceed the flow rate of oxygen or oxygen-enriched air and there is little or no provision for rebreathing, patients often inhale variable (and poorly controlled) quantities of room air with each breath.

Room air leaks into relatively loosely fitting face shields and masks during part of each inspiration, and excess fresh gas (that is, oxygen or oxygen-enriched air) together with exhaled gas leaks out in a similar manner during exhalation. Thus, conventional oxygen supplementation systems are relatively wasteful of oxygen (much of which is lost to the ambient atmosphere instead of benefiting the patient). An additional disadvantage of face shields and loose-fitting masks is that they are of little use for assisting or controlling ventilation if the patient experiences respiratory arrest requiring resuscitation.

Relatively loose-fitting face shields and masks also represent an added expense when they replace an anesthesia mask on patients being transported from an operating room to a recovery room or intensive care unit. The added expense may be justified in current practice, however, because the T-piece and rebreathing tube (or analogous apparatus) needed to conventionally adapt anesthesia masks for transport of spontaneously breathing patients are relatively bulky and include respiratory dead space which may be detrimental to some patients. Thus, a relatively compact and inexpensive adaptor for use with an anesthesia mask in a patient transport system would be a desirable alternative to the currently available supplemental oxygen transport equipment described above.

SUMMARY OF THE INVENTION

The invention comprises a system to provide supplemental oxygen to a spontaneously breathing patient via a close-fitting oronasal mask such as the masks used to support and/or assist ventilation during anesthesia. Such a system can be easily implemented for patients being transported from an operating room to a recovery room or intensive care unit. By quickly and inexpensively adapting conventional anesthesia masks for a new role in providing supplemental oxygen, often but not exclusively in a transport environment, the invention offers a way to enhance patient safety and shorten recovery time while conserving oxygen (relative to the demands of conventional oxygen supplementation systems). Oxygen conservation is achieved by ensuring substantially complete delivery of fresh gas flows into the mask (with relatively small mounts being carried out by an exiting gas stream), and by substantial reduction of leaks around mask edges due to the anatomically conforming nature of masks such as those used for administering anesthesia.

During use of the invention, oxygen-enriched fresh gas (typically substantially pure oxygen or ambient air to which oxygen has been added) is carried to the oronasal mask through an oxygenation adaptor, the mask connector portion of which preferably fits slidingly and sealingly into the mask connector orifice (usually a circular orifice 22 mm in diameter and substantially formed within the thickness of the mask body). The adaptor allows simultaneous flow of fresh gas into the mask and exhaled gas out of the mask through the mask connector orifice. Because a fresh gas outlet is located substantially within (including slightly distal to or slightly proximal to) the mask connector portion of the adaptor, a fresh gas flow is substantially delivered into the mask while a relatively small component of the fresh gas flow is available in the region of the mask connector to facilitate relatively smooth gas flow out of the mask during exhalation as explained below. Countercurrent flow of fresh (oxygen-enriched) gas and exhaled gas thus takes place through the same orifice, but with minimal mixing of the two gas streams. Consequently, most fresh gas passing through the fresh gas outlet actually enters the mask (that is, moves into the mask significantly beyond the mask connector orifice) where it can mix with and displace other gas already there. This action has the effect of raising the oxygen content of gas within the mask even during exhalation, the gas remaining after exhalation being substantially that which enters the patient's airway first on the next inhalation. Since relatively small amounts of fresh gas are carried away with the exhaled gas before entering the mask, the fresh gas oxygen content is substantially preserved for use in raising the oxygen content of gas within the mask. Thus, supplemental oxygen flow rates needed to obtain a predetermined increase in $FiO_2$ for a patient can be set relatively lower than would be necessary in systems wherein significant mixing of fresh and exhaled gases occurs outside of the mask connector orifice (that is, significantly before entry into the mask, as in a Bain circuit or a Mapleson B or C circuit).

Mixing of fresh gas and exhaled gas streams in the oxygenation adaptor of the present invention is minimized by substantial physical separation of the gas streams as they pass through the mask connector region of the adaptor. In preferred embodiments, this separation is facilitated by locating a fresh gas outlet substantially centrally (that is, substantially coaxially) within the mask connector portion. The slightly higher-than-ambient pressure ahead of the (preferably substantially axially moving) fresh gas stream within the mask connector portion tends to divert any exiting gas stream toward the substantially cylindrical wall of the mask connector portion where the Coanda effect then tends to cause wall attachment of the exhaled gas stream in a substantially cylindrical flow pattern. Relatively small amounts of fresh gas available from a substantially centrally moving fresh gas stream in the mask connector portion can move laterally (that is, toward the connector portion wall) to be entrained by the exiting gas stream. This relatively small lateral gas flow allows the Coanda effect to persist substantially throughout the mask connector portion, forming the exiting gas stream into a substantially cylindrical shell of finite thickness wherein most of the exiting gas stream is effectively separated from the countercurrent stream of incoming fresh gas. This effective separation of countercurrent gas streams minimizes mixing of the two streams and thus facilitates the efficient delivery of fresh gas through the mask connector portion of the oxygenation adaptor and into the mask even during exhalation.

To accomplish the above actions during use with an oronasal mask, the oxygenation adaptor of the present invention comprises a substantially hollow rebreathing chamber having an internal volume and a room air port sealingly coupled (as by molding, gluing or welding) to the rebreathing chamber and communicating with the rebreathing chamber internal volume. The rebreathing chamber may be substantially cylindrical, having a first end, a second end, and an axis substantially centered and extending between said first and second ends.

A substantially hollow and substantially cylindrical mask connector portion of the adaptor (preferably having a 22 mm outside diameter) has a first end, a second end, and an axis substantially centered and extending between the first and second connector portion ends. The mask connector portion first end is sealingly coupled to the rebreathing chamber and communicates with the rebreathing chamber internal volume for coupling the rebreathing chamber to an oronasal mask. Where the rebreathing chamber is substantially cylindrical, the rebreathing chamber axis may preferably be substantially collinear with the connector portion axis.

Additionally, the oxygenation adaptor comprises an elongated tubular fresh gas injection means comprising a longitudinal fresh gas channel. The longitudinal fresh gas channel has a proximal fresh gas inlet and at least one distal fresh gas outer, at least one distal fresh gas outlet being within or proximate to the mask connector portion. The longitudinal fresh gas channel may be of any size and length compatible with the fresh gas supply to be used, but it preferably comprises a distal portion substantially coaxial with the mask connector portion axis.

Note that the preferred position of at least one distal fresh gas outlet may be proximate the mask connector portion first end or (more preferably) the second end (or at a predetermined position between the first and second ends). For any given application, the most preferred position may be empirically determined as a function of, for example, the fresh gas flow rate, the patient's minute ventilation, and the maximum exiting gas flow rate through the mask connector portion.

Note also that while the design of the oxygenation adaptor minimizes turbulence in an exiting gas stream to minimize mixing of fresh gas and exiting gas streams, turbulence may be preferred in an entering gas stream comprising room air which passes through the room air port to encourage substantially uniform oxygen enrichment of the gas subsequently breathed by a patient. Thus the room air port may comprise flow directing means (such as a plurality of vanes) to facilitate substantially spiral or otherwise turbulent gas flow in the rebreathing chamber.

The present invention also comprises an oronasal mask oxygen transport system comprising a compatible embodiment of the above oxygenation adaptor and an oronasal mask having a connector orifice with an inside diameter of approximately 22 mm, the mask connector portion being slidingly fitted within the mask connector orifice.

A further embodiment of the invention comprises a method of providing oxygen-enriched gas to an oronasal mask. The method comprises sealingly connecting the above oxygenation adaptor to an oronasal mask using the mask connector portion and then directing pressurized oxygen-enriched gas into the fresh gas inlet. This method complements a method of providing oxygen-enriched gas to a spontaneously breathing patient, the latter method comprising fitting an oronasal mask to the patient and connecting the above oxygenation adaptor to the oronasal mask using the mask connector portion, followed by direction of pressurized oxygen-enriched gas into the fresh gas inlet.

DETAILED DESCRIPTION

Figure 1:
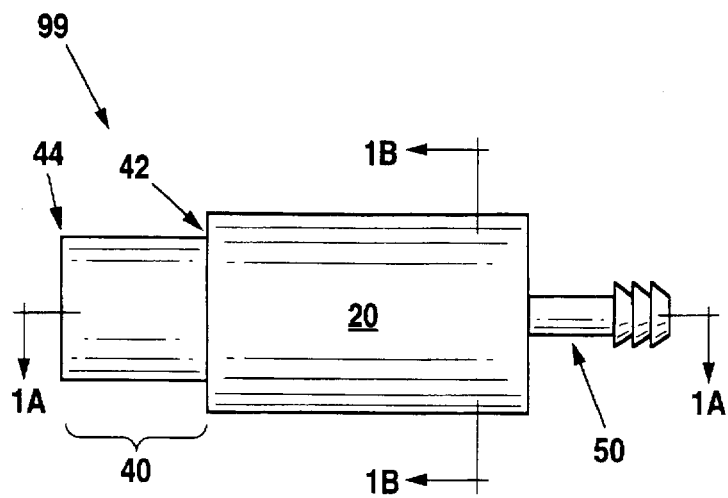
FIG. 1 schematically illustrates an oxygenation adaptor for use with an anesthesia mask in a transport system.
Figure 1B:
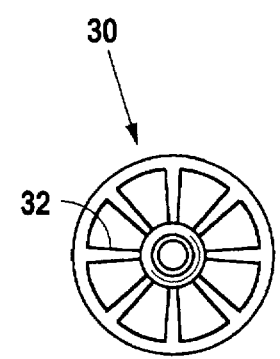
FIG. 1B schematically illustrates a transverse cross-section of the oxygenation adaptor of FIG. 1.
Figure 1A:
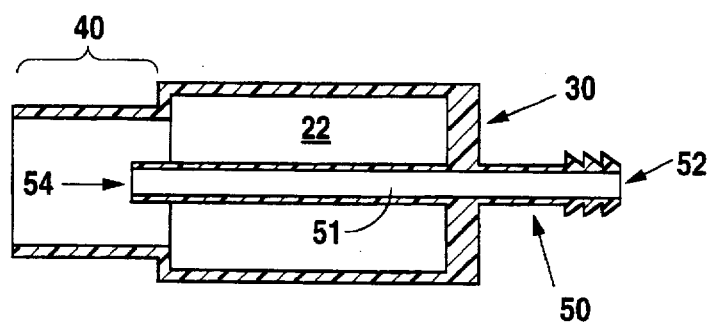
FIG. 1A schematically illustrates a longitudinal cross-section of the oxygenation adaptor of FIG. 1.

FIGS. 1, 1A, 1B schematically illustrate an oxygenation adaptor 99 for an oronasal mask. The adaptor comprises a substantially hollow rebreathing chamber 20 having an internal volume 22 and a room air port 30 sealingly coupled (typically molded into) rebreathing chamber 20 and communicating with rebreathing chamber internal volume 22. A substantially hollow and substantially cylindrical mask connector portion 40 has a first end 42, a second end 44, and an axis substantially centered and extending between first and second connector portion ends 42,44 respectively. Mask connector portion first end 42 is sealingly coupled (typically by molding, gluing or welding) to rebreathing chamber 20 and communicates with rebreathing chamber internal volume 22 for coupling rebreathing chamber 20 to an oronasal mask. Elongated tubular fresh gas injection means 50 comprises a longitudinal fresh gas channel 51 having a proximal fresh gas inlet 52 and at least one distal fresh gas outlet 54. At least one distal fresh gas outlet 54 is substantially within mask connector portion 40, but may be proximate mask connector portion first end 42 or proximate mask connector portion second end 44 or between first end 42 and second end 44.

Figure 2:
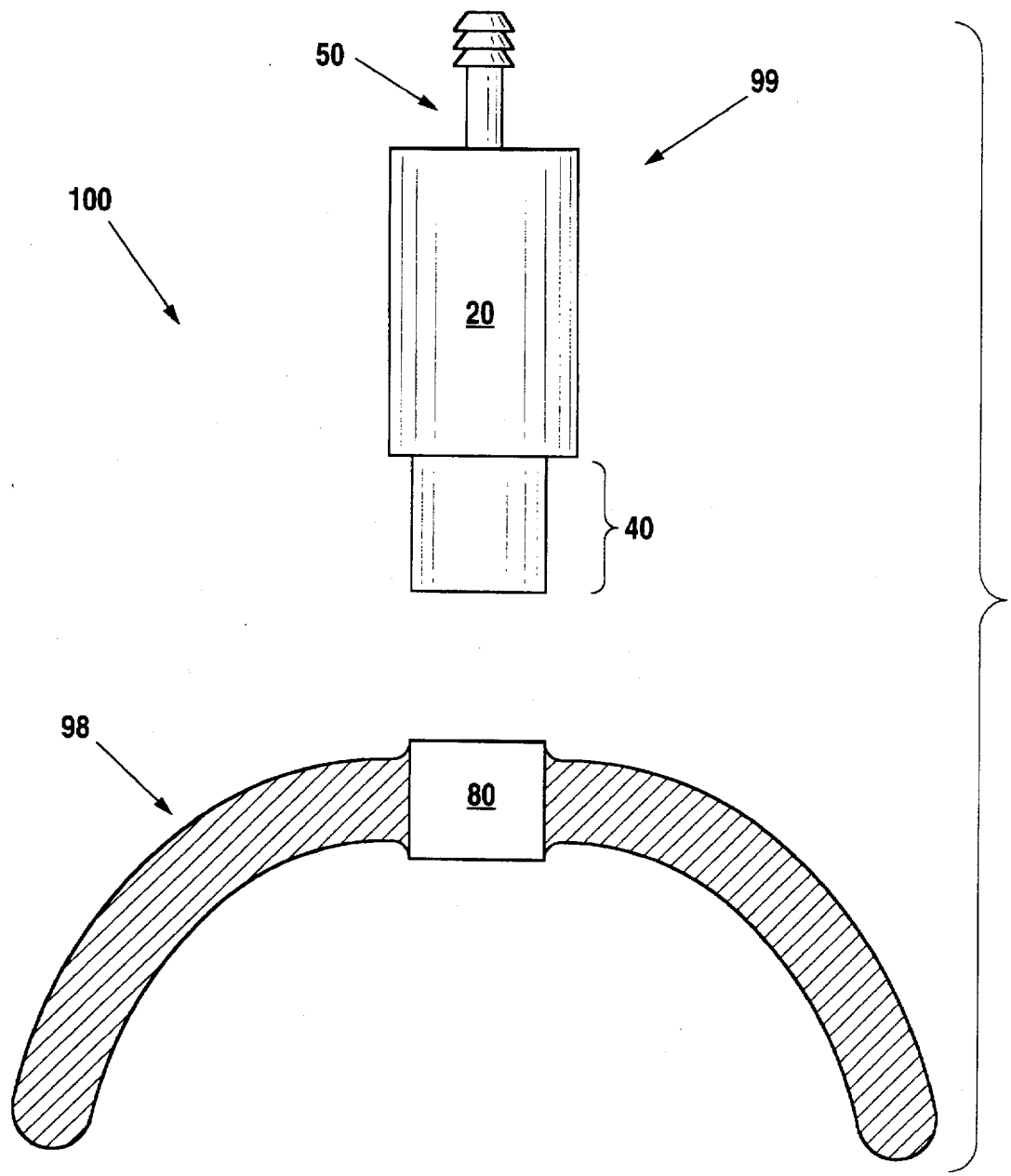
FIG. 2 schematically illustrates an exploded view of an oronasal mask oxygen transport system comprising the oxygenation adaptor of FIG. 1 an anesthesia mask (cross-section view).

Oxygenation adaptor 99 may comprise a room air port 30 which itself comprises flow directing means 32 (such as, for example, a plurality of vanes) to facilitate substantially spiral gas flow turbulence in rebreathing chamber 22 to facilitate mixing of the turbulent entering air with fresh gas as the turbulent air passes distal fresh gas outlet 54 while flowing into a mask 98 (see FIG. 2).

An oronasal mask oxygen transport system 100 is schematically illustrated in FIG. 2, the system comprising the oxygenation adaptor 99 and an oronasal mask 98 having a connector orifice 80 with an inside diameter of approximately 22 mm. Mask connector portion 40 fits slidingly and sealingly within said mask connector orifice 80.

What is claimed is:

1. An oxygenation adaptor for an oronasal mask, the adaptor comprising a substantially hollow rebreathing chamber having an internal volume;

a room air port sealingly coupled to said rebreathing chamber and communicating with said rebreathing chamber internal volume;

a substantially hollow and substantially cylindrical mask connector portion having a first end, a second end, and an axis substantially centered and extending between said first and second connector portion ends, said mask connector portion first end being sealingly coupled to said rebreathing chamber and communicating with said rebreathing chamber internal volume for coupling said rebreathing chamber to an oronasal mask, said mask having a thickness;

elongated tubular fresh gas injection means comprising a longitudinal fresh gas channel, said longitudinal fresh gas channel having a proximal fresh gas inlet and at least one distal fresh gas outlet, each said distal fresh gas outlet being substantially within said mask connector portion, and substantially within said thickness of said mask, for delivering a fresh gas flow substantially into the mask.

2. The oxygenation adaptor of claim 1 wherein at least one said distal fresh gas outlet is proximate said mask connector portion first end.

3. The oxygenation adaptor of claim 1 wherein at least one said distal fresh gas outlet is proximate said mask connector portion second end.

4. The oxygenation adaptor of claim 1 wherein said rebreathing chamber is substantially cylindrical, having a first end, a second end, and an axis substantially centered and extending between said first and second ends.

5. The oxygenation adaptor of claim 4 wherein said rebreathing chamber axis is substantially collinear with said connector portion axis.

6. The oxygenation adaptor of claim 1 wherein said longitudinal fresh gas channel comprises a distal portion substantially coaxial with said mask connector portion axis.

7. The oxygenation adaptor of claim 1 wherein said room air port comprises flow directing means to facilitate substantially spiral gas flow in said rebreathing chamber.

8. The oxygenation adaptor of claim 1 wherein said mask connector portion has an outside diameter of approximately 22 mm.

9. An oronasal mask oxygen transport system, the system comprising the oxygenation adaptor of claim 8; and an oronasal mask having a connector orifice with an inside diameter of approximately 22 mm, said mask connector portion being slidingly and sealingly fitted within said mask connector orifice.

10. A method of providing oxygen-enriched gas to an oronasal mask, the method comprising sealingly connecting the oxygenation adaptor of claim 1 to the oronasal mask using said mask connector portion; and directing pressurized oxygen-enriched gas into said fresh gas inlet.

11. A method of providing oxygen-enriched gas to a spontaneously breathing patient, the method comprising fitting an oronasal mask to the patient;

connecting the oxygenation adaptor of claim 1 to said oronasal mask using said mask connector portion; and directing pressurized oxygen-enriched gas into said fresh gas inlet.

\* \* \* \* \*